(12) United States Patent
Tsutsui

(10) Patent No.: US 11,297,257 B2
(45) Date of Patent: Apr. 5, 2022

(54) IMAGE PICKUP SYSTEM

(71) Applicant: OLYMPUS CORPORATION, Tokyo (JP)

(72) Inventor: Keisuke Tsutsui, Kawaguchi (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 17/104,246

(22) Filed: Nov. 25, 2020

(65) Prior Publication Data

US 2021/0105395 A1    Apr. 8, 2021

Related U.S. Application Data

(63) Continuation of application No. PCT/JP2019/007603, filed on Feb. 27, 2019.

(30) Foreign Application Priority Data

May 29, 2018 (JP) .............................. JP2018-102346

(51) Int. Cl.
*H04N 5/77* (2006.01)
*H04N 5/235* (2006.01)
(Continued)

(52) U.S. Cl.
CPC ....... *H04N 5/2354* (2013.01); *A61B 1/00006* (2013.01); *A61B 1/00009* (2013.01);
(Continued)

(58) Field of Classification Search
None
See application file for complete search history.

(56) References Cited

U.S. PATENT DOCUMENTS

2008/0136950 A1    6/2008  Nakajima
2014/0194686 A1*   7/2014  Murayama ........... H04N 5/3532
                                                          600/109

(Continued)

FOREIGN PATENT DOCUMENTS

EP        1924079 A2    5/2008
JP    2008-131127 A     6/2008
(Continued)

OTHER PUBLICATIONS

International Search Report dated May 14, 2019 issued in PCT/JP2019/007603.

*Primary Examiner* — Eileen M Adams
(74) *Attorney, Agent, or Firm* — Scully, Scott, Murphy & Presser, P.C.

(57) ABSTRACT

An image pickup system includes an image pickup apparatus, and an information processing apparatus connectable with the image pickup apparatus. The image pickup apparatus includes an effective pixel area including a plurality of effective pixels configured to output accumulated electric charge as an image signal, a global reset circuit configured to output a global reset signal, and a reading timing generation circuit configured to temporarily stop and resume, at optional timings, reading of the electric charge accumulated by the effective pixels included in each of a plurality of divided areas. The information processing apparatus detects brightness of an object based on the image signals, and determines, based on the brightness detection signal, the number of the plurality of divided areas, a timing of reading the electric charge accumulated by the effective pixels included in each of the plurality of divided areas, and a timing of outputting the global reset signal.

8 Claims, 3 Drawing Sheets

(51) Int. Cl.
*A61B 1/00* (2006.01)
*A61B 1/06* (2006.01)
*H04N 5/225* (2006.01)
*H04N 5/76* (2006.01)

(52) U.S. Cl.
CPC ........ *A61B 1/00045* (2013.01); *A61B 1/0661* (2013.01); *H04N 5/2256* (2013.01); *H04N 5/2351* (2013.01); *H04N 5/76* (2013.01); *H04N 2005/2255* (2013.01)

(56) References Cited

U.S. PATENT DOCUMENTS

2014/0239188 A1\* 8/2014 Tezuka ................. A61B 6/4233
250/394
2014/0316196 A1 10/2014 Wichern et al.
2016/0360948 A1\* 12/2016 Mizuno ................. A61B 1/045

FOREIGN PATENT DOCUMENTS

| JP | 2011-206336 A | 10/2011 |
| JP | 2016-39494 A | 3/2016 |
| JP | 2016-512994 A | 5/2016 |
| JP | 2017-32881 A | 2/2017 |
| WO | WO 2014/134501 A2 | 9/2014 |

\* cited by examiner

IMAGE PICKUP SYSTEM

CROSS REFERENCE TO RELATED APPLICATION

This application is a continuation application of PCT/JP2019/007603 filed on Feb. 27, 2019 and claims benefit of Japanese Application No. 2018-102346 filed in Japan on May 29, 2018, the entire contents of which are incorporated herein by this reference.

BACKGROUND OF THE INVENTION

1. Field of the Invention

The present invention relates to an image pickup system.

2. Description of the Related Art

Conventionally, an endoscope system including an endoscope configured to pick up an image of an object inside a subject and a processor configured to generate an observation image of the object picked up by the endoscope has been widely used in medical and industrial fields and the like.

An endoscope in which, for example, a CMOS image pickup device is employed as a solid image pickup device and an image pickup signal (video data) outputted from the CMOS image pickup device is transmitted to an image processing apparatus at a later stage is widely known as the endoscope in such an endoscope system.

The image pickup device such as the above-described CMOS image pickup device is typically driven by receiving supply of a predetermined power voltage and a control signal from the image processing apparatus through a cable disposed in an insertion portion of the endoscope and a universal code. In addition, the image pickup signal (video data) outputted from the image pickup device is forwarded through the cable toward a connector portion disposed at a proximal end portion of the insertion portion and toward the image processing apparatus.

The CMOS image pickup device mounted on such an endoscope system is disposed at the distal end of the insertion portion of the endoscope, and thus a small-sized CMOS image pickup device is used. The small-sized CMOS image pickup device includes a small number of lines, and thus cannot perform exposure control at a sufficient resolution even through an electronic shutter mounted thereon.

Thus, in the conventional endoscope system, exposure control of the endoscope on which the small-sized CMOS image pickup device is mounted is performed by controlling the brightness of illumination light from a light source. Japanese Patent Application Laid-Open Publication No. 2011-206336 discloses an endoscope system in which the exposure durations of all pixel rows are made equal to each other by controlling a global reset signal and an illumination duration (exposure time period).

In the conventional endoscope system, a medical treatment laser apparatus for performing medical treatment through irradiation with a visible light laser beam such as a KTP laser beam or an invisible light laser beam such as a YAG laser beam is additionally used in some cases.

SUMMARY OF THE INVENTION

An image pickup system according to an aspect of the present invention is an image pickup system including: a light source configured to irradiate an object with illumination light, an image pickup apparatus configured to pick up an image of the object, and an information processing apparatus that is connectable with the image pickup apparatus. The image pickup apparatus includes an effective pixel area including a plurality of effective pixels disposed in a two-dimensional matrix and each configured to receive light from outside, accumulate the light as electric charge, and output the accumulated electric charge as an image signal, a global reset circuit configured to output a global reset signal for resetting the electric charge accumulated by the effective pixels, and a reading timing generation circuit configured to temporarily stop and resume, at optional timings, reading of the electric charge accumulated by the effective pixels included in each of a plurality of divided areas into which the effective pixel area is divided. The information processing apparatus receives the image signals read from the image pickup apparatus, temporarily stores the image signals in a memory, connects and outputs the image signals read from the plurality of divided areas, detects brightness of the object based on the image signals, outputs a brightness detection signal, and determines, based on the brightness detection signal, the number of the plurality of divided areas, a timing of reading the electric charge accumulated by the effective pixels included in each of the plurality of divided area, and a timing of outputting the global reset signal.

DETAILED DESCRIPTION OF THE PREFERRED EMBODIMENT

An embodiment of the present invention will be described below with reference to the accompanying drawings.

Figure 1:
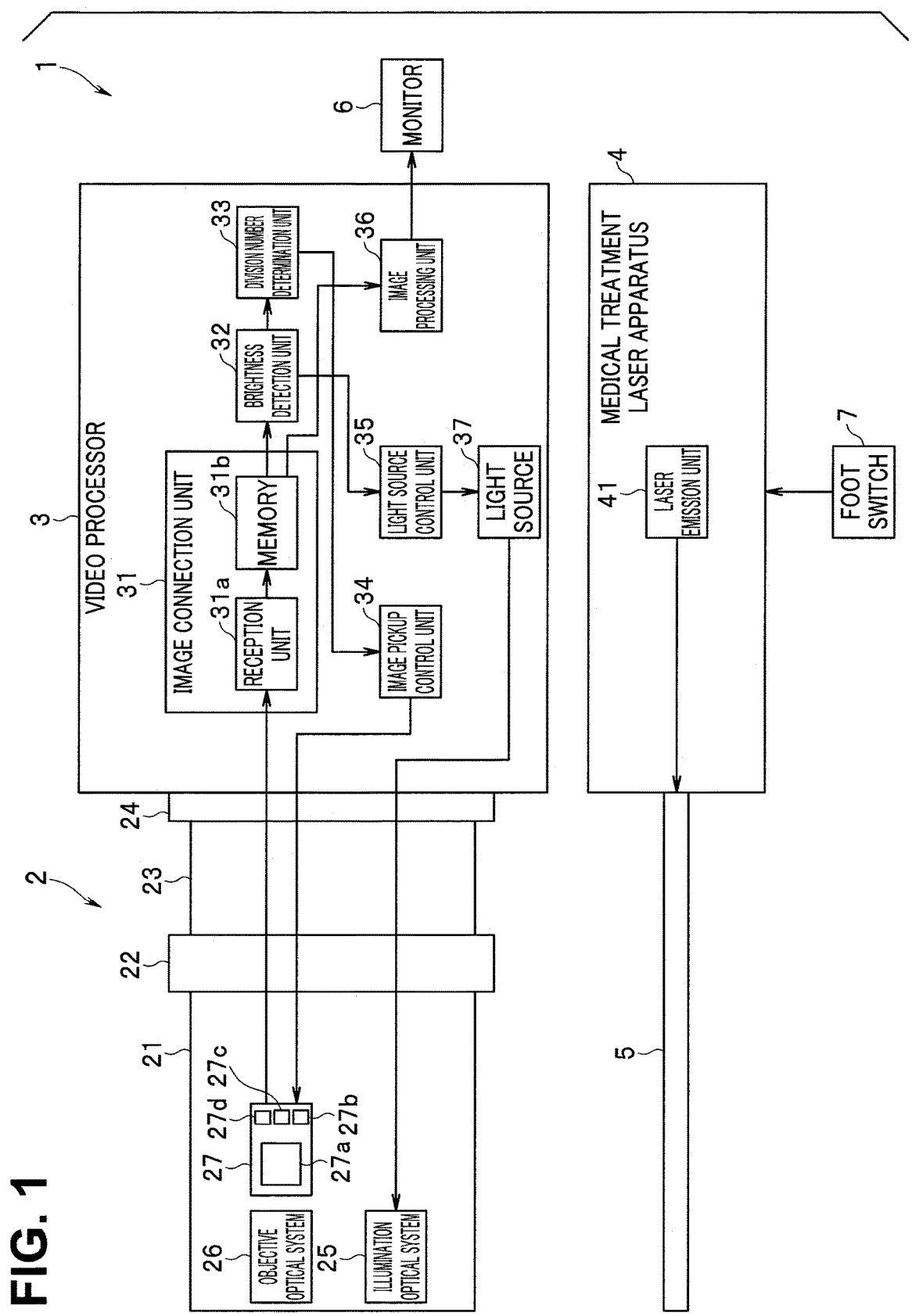
FIG. 1 is a diagram illustrating an exemplary entire configuration of an endoscope system according to an embodiment of the present invention.

FIG. 1 is a diagram illustrating an exemplary entire configuration of an endoscope system according to the embodiment of the present invention.

This endoscope system 1 includes an endoscope 2, a video processor 3, a medical treatment laser apparatus 4, a laser probe 5, and a monitor 6.

The endoscope 2 includes an insertion portion 21 to be inserted into a subject, an operation portion 22 provided at the proximal end of the insertion portion 21, a universal code 23 extending from the operation portion 22, and a connector 24 provided at the proximal end of the universal code 23.

The insertion portion 21 includes, from the distal end side, a distal end portion, a bending portion, and a flexible tube portion. An illumination optical system 25, an objective optical system 26, and a CMOS image pickup apparatus 27 configured by a CMOS image pickup device are provided at the distal end portion of the insertion portion 21.

The illumination optical system 25 irradiates an object in the subject with illumination light generated by a light source 37 to be described later through a distal end surface of the distal end portion of the insertion portion 21. The objective optical system 26 forms an optical image of the object illuminated with the illumination light.

The CMOS image pickup apparatus 27 includes: an effective pixel area 27a including a plurality of effective pixels disposed in a two-dimensional matrix and each configured to receive light from outside, accumulate the light as electric charge, and output the accumulated electric charge as an image signal; a global reset circuit 27b configured to output a global reset signal for resetting the electric charge accumulated by the effective pixels in the effective pixel area 27a; a reading timing generation circuit 27c capable of temporarily stopping and resuming, at optional timings, reading of the electric charge in divided areas into which the area of the effective pixels in the effective pixel area 27a is divided; and a timing generation circuit 27d configured by a timing generator (TG) configured to generate a drive timing signal (vertical synchronizing signal VD) of the CMOS image pickup apparatus 27.

The video processor 3 as an information processing apparatus includes an image connection unit 31, a brightness detection unit 32, a division number determination unit 33, an image pickup control unit 34, a light source control unit 35, an image processing unit 36, and the light source 37. The image connection unit 31 includes a reception unit 31a and a memory 31b. Note that the light source 37 may be provided at a light source apparatus provided separately from the video processor 3.

The medical treatment laser apparatus 4 includes a laser emission unit 41 configured to emit a medical treatment laser beam. The medical treatment laser apparatus 4 is connected with the laser probe 5 and a foot switch 7.

An operation signal is inputted to the medical treatment laser apparatus 4 when an operator steps on (operating) the foot switch 7 as necessary. Having received the operation signal, the laser emission unit 41 of the medical treatment laser apparatus 4 emits a laser beam. The laser beam emitted from the laser emission unit 41 is incident on a proximal end portion of the laser probe 5 and then emitted from a distal end portion of the laser probe 5.

In this manner, the medical treatment laser apparatus 4 can emit a laser beam for an optional duration at an optional timing by the operator. Note that the laser probe 5 may be inserted into a forceps channel (not illustrated) of the insertion portion 21 and used while protruding from the distal end portion of the insertion portion 21.

An image signal outputted from the effective pixel area 27a is received by the reception unit 31a and then temporarily stored in the memory 31b. The image connection unit 31 connects the image signals for one frame stored in the memory 31b and outputs the image signals to the brightness detection unit 32 and the image processing unit 36.

The brightness detection unit 32 detects the brightness of the object based on the image signals outputted from the image connection unit 31 and outputs a brightness detection signal to the division number determination unit 33 and the light source control unit 35.

The division number determination unit 33 determines, based on the brightness detection signal outputted from the brightness detection unit 32, the number of a plurality of divided areas into which the effective pixel area 27a is divided, the timing of reading the electric charge accumulated by the effective pixels included in each of the plurality of divided areas, and the timing of outputting the global reset signal outputted from the global reset circuit 27b, and outputs the number and the timings to the image pickup control unit 34.

The image pickup control unit 34 as a transmission circuit controls the CMOS image pickup apparatus 27 by transmitting, to the CMOS image pickup apparatus 27, parameters for controlling the number of divided areas of the effective pixel area 27a, which is determined by the division number determination unit 33, the timing of reading the electric charge accumulated by the effective pixels in each divided area, and the timing of outputting the global reset signal$_o$ The light source control unit 35 calculates a target illuminance value of the light source 37 as an illumination unit based on the brightness detection signal outputted from the brightness detection unit 32, and controls the emission amount, the emission time period, and the emission timing of the illumination light emitted from the light source 37.

The light source 37 is configured by a lamp, light emission from which is controllable for an optional duration based on control by the light source control unit 35. Note that the light source 37 is not limited to such a lamp but may be, for example, an LED.

The image processing unit 36 provides predetermined image processing on the image signals inputted through the brightness detection unit 32, generates an image of the object, and outputs the image to the monitor 6. When the brightness of the object detected by the brightness detection unit 32 is low, the image processing unit 36 performs automatic gain control (AGC) or image processing (image correction) of removing accumulation of the electric charge by the medical treatment laser apparatus 4. Accordingly, an observation image obtained by the endoscope 2 is displayed on the monitor 6.

Operation of the endoscope system thus configured will be described below.

First, normal operation of the endoscope system 1 will be described. The normal operation is operation in which reading is performed without dividing an effective pixel area of the effective pixel area 27a.

Figure 2:
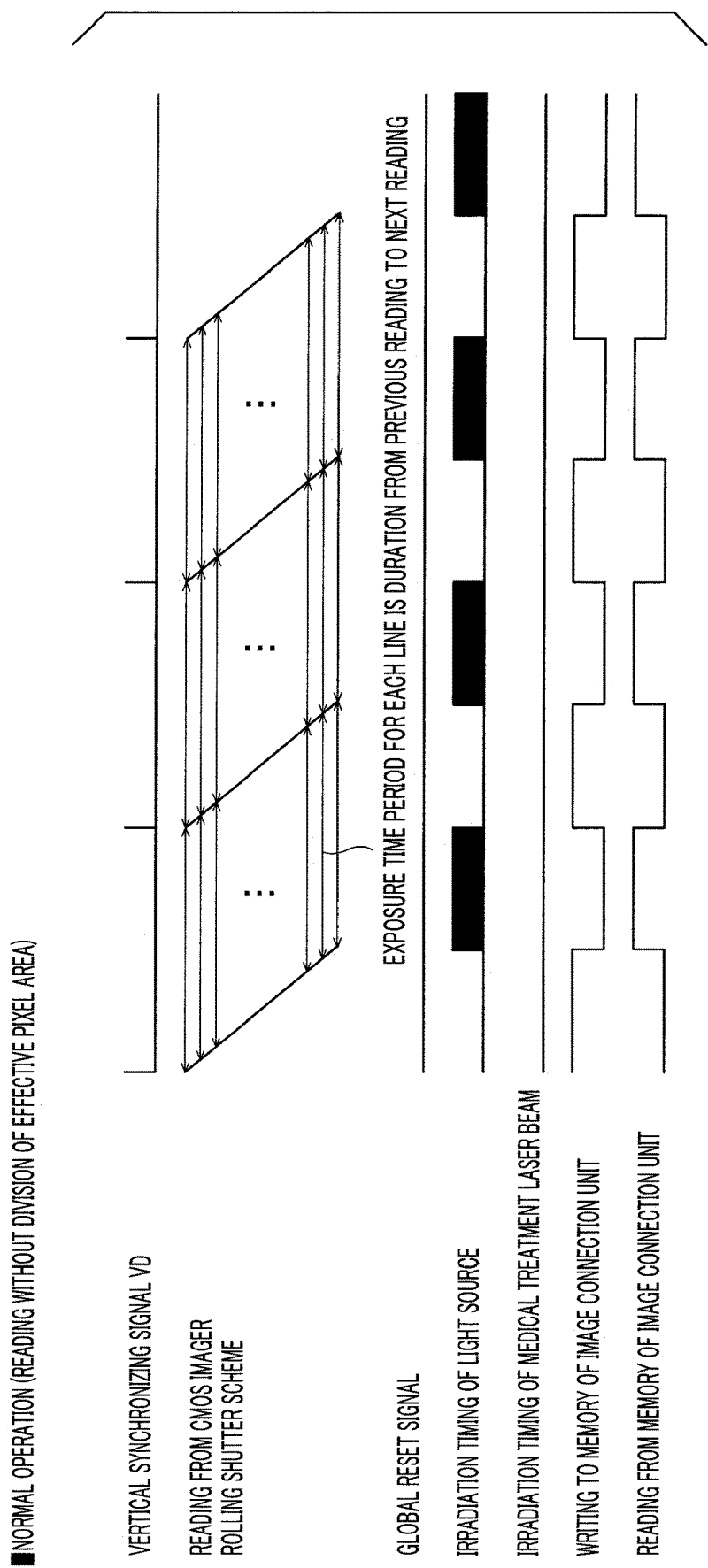
FIG. 2 is a timing chart for description of exemplary normal operation of the endoscope system.

FIG. 2 is a timing chart for description of exemplary normal operation of the endoscope system.

The normal operation of the endoscope system 1 is executed, for example, when a medical treatment laser beam is not emitted from the medical treatment laser apparatus 4 and a detected value of the brightness of the object detected by the brightness detection unit 32 is smaller than a predetermined threshold value.

The normal operation of the endoscope system 1 generates an image by a typical rolling shutter scheme in which exposure and reading are performed at timings shifted for each line of the effective pixel area 27a. In this case, an exposure time period for each line is the duration from the previous reading to the next reading. In the normal operation, the global reset signal is not inputted from the global reset circuit 27b.

The image signals read for each line are sequentially written to the memory 31b of the image connection unit 31 and connected. Thereafter, the image signals of one frame written to the memory 31b are connected and outputted to the brightness detection unit 32 and the image processing unit 36.

Next, divided reading operation will be described. The divided reading operation is operation in which reading is performed by dividing the effective pixel area of the effective pixel area 27a.

Figure 3:
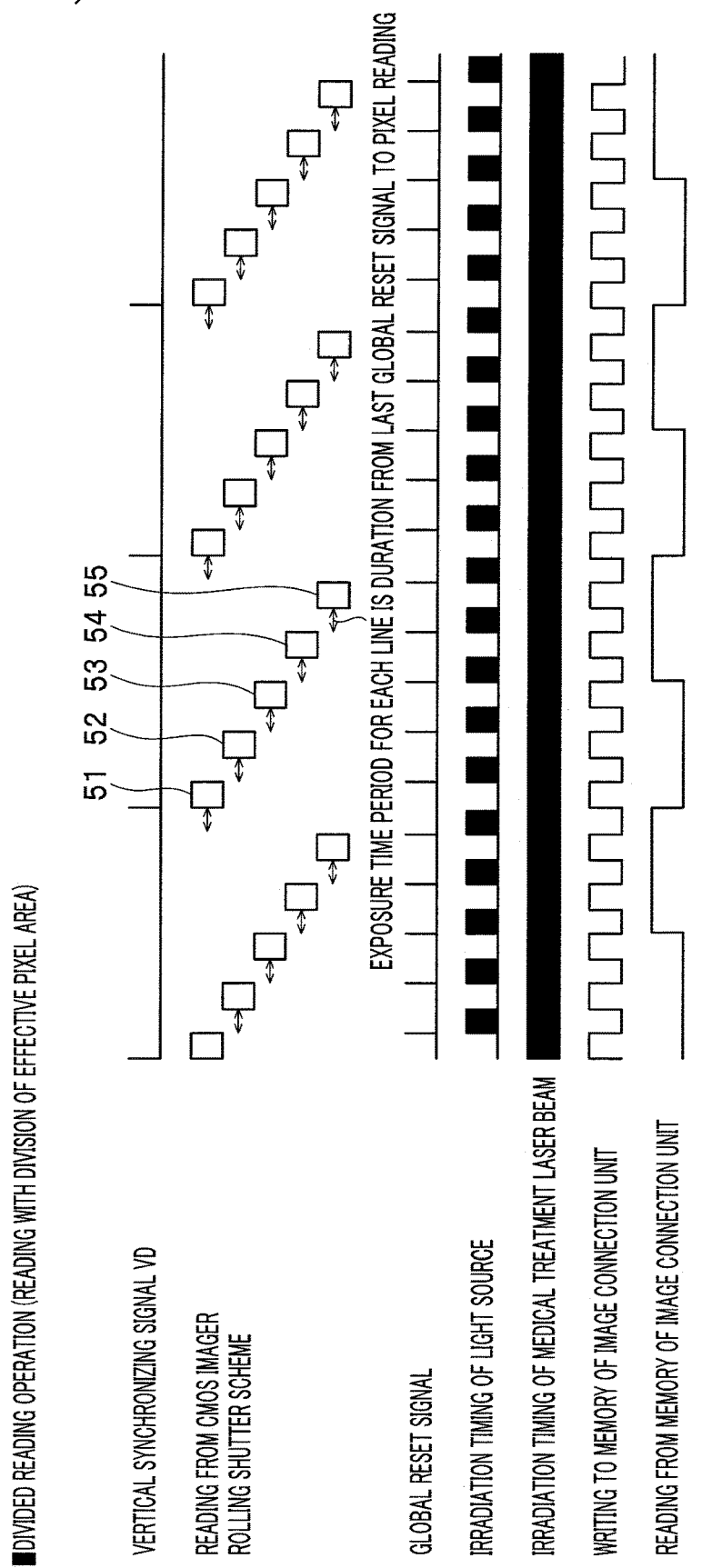
FIG. 3 is a timing chart for description of exemplary divided reading operation of the endoscope system.

FIG. 3 is a timing chart for description of exemplary divided reading operation of the endoscope system.

The divided reading operation of the endoscope system 1 is executed, for example, when a medical treatment laser beam is emitted from the medical treatment laser apparatus 4 and the detected value of the brightness of the object detected by the brightness detection unit 32 is equal to or larger than the predetermined threshold value.

A medical treatment laser beam is emitted from the laser emission unit 41 of the medical treatment laser apparatus 4 when the operator steps on the foot switch 7. The medical treatment laser beam is emitted from the distal end of the laser probe 5. In this case, the amount of light is increased by the illumination light from the light source 37 and the medical treatment laser beam from the laser emission unit 41, and electric charge saturation potentially occurs in the effective pixel area 27a.

Thus, the division number determination unit 33 determines, based on brightness information detected by the brightness detection unit 32, the number of divided areas from which reading is performed as an image pickup area in the effective pixel area 27a, the timing of reading, and the timing of global resetting.

The example illustrated in FIG. 3 corresponds to a case in which the effective pixel area 27a is divided into five divided areas 51 to 55. For example, when the number of lines in the effective pixel area 27a is 100, the divided areas 51 to 55 each have 20 lines. Note that although the effective pixel area 27a is divided into the five divided areas 51 to 55 in FIG. 3, the number of divided areas is not limited to five but may be four or less or may be six or more.

For example, when determining the number of divided areas in the effective pixel area 27a based on the brightness information detected by the brightness detection unit 32, the division number determination unit 33 performs control to increase the number of divided areas as the brightness of the object detected by the brightness detection unit 32 increases.

Then, the reading timing generation circuit 27c performs control to temporarily stop and resume, at optional timings, reading of the electric charge accumulated by the effective pixels in the divided areas 51 to 55. Specifically, reading operation is stopped once lines 1 to 20 in the divided area 51 are sequentially read. Then, the global reset signal is inputted from the global reset circuit 27b to reset the electric charge accumulated in the effective pixel area 27a.

After the global reset signal is inputted, a predetermined exposure time period is provided to accumulate electric charge in the effective pixel area 27a. Accordingly, the exposure time period for each line is the duration from the last global reset signal to pixel reading. Thereafter, reading is resumed from lines 21 to 40 in the divided area 52, which is next to the divided area 51.

In this case, the timing generation circuit 27d is not reset by the global reset signal. Accordingly, reading is resumed at the first line in the divided area 52 (the twenty-first line in the entire effective pixel area 27a). Thereafter, the same divided reading operation is executed in the order of the divided area 53, the divided area 54, and the divided area 55. Image signals intermittently read in the order of the divided areas 51 to 55 are sequentially written to the memory 31b of the image connection unit 31 and connected. Thereafter, the image signals of one frame written to the memory 31b are connected and outputted to the brightness detection unit 32 and the image processing unit 36.

As described above, each time lines in the divided areas 51 to 55 are read, the endoscope system 1 stops pixel reading and inputs the global reset signal to reset electric charge accumulated in the effective pixel area 27a. Thereafter, the endoscope system 1 performs exposure in a duration until the next pixel reading, and then resumes reading.

As a result, the endoscope system 1 can perform exposure control while canceling electric charge accumulation due to a medical treatment laser beam emitted from the medical treatment laser apparatus 4. For example, when pixels of lines in the divided area 52 are to be read, electric charge of a medical treatment laser beam emitted in the short duration from inputting of the last global reset signal to the next pixel reading is accumulated. Accordingly, electric charge saturation does not occur in the effective pixel area 27a when the light source 37 and the medical treatment laser apparatus 4 are simultaneously used.

Thus, according to the endoscope system of the present embodiment, it is possible to prevent electric charge saturation at the CMOS image pickup apparatus and obtain an image having no electric charge saturation through irradiation with a non-self-emitted medical treatment laser beam.

The present invention is not limited to the above-described embodiment but may be, for example, changed or modified in various kinds of manners without departing from the gist of the present invention.

What is claimed is:

1. An image pickup system comprising:
  a light source configured to irradiate an object with illumination light;
  an image pickup apparatus configured to pick up an image of the object; and
  an information processing apparatus that is connectable with the image pickup apparatus,
  wherein the image pickup apparatus comprises:
    an effective pixel area including a plurality of effective pixels disposed in a two-dimensional matrix and each configured to receive light from outside, accumulate the light as electric charge, and output the accumulated electric charge as an image signal;
    a global reset circuit configured to output a global reset signal for resetting the electric charge accumulated by the effective pixels; and
    a reading timing generation circuit configured to temporarily stop and resume, at optional timings, reading of the electric charge accumulated by the effective pixels included in each of a plurality of divided areas into which the effective pixel area is divided, and
  wherein the information processing apparatus is configured to:
    receive the image signals read from the image pickup apparatus, temporarily store the image signals in a memory, connect and output the image signals read from the plurality of divided area;
    detect brightness of the object based on the image signals, and output outputs a brightness detection signal; and
    determine, based on the brightness detection signal, the number of the plurality of divided areas, a timing of reading the electric charge accumulated by the effective pixels included in each of the plurality of divided area, and a timing of outputting the global reset signal; and
    perform, when determining the number of the plurality of divided areas, control to increase the number of divided areas as the brightness of the object increases, based on the brightness detection signal.

2. The image pickup system according to claim 1,
  wherein the reading timing generation circuit is configured to temporarily stop reading of the electric charge after reading the electric charge from the effective pixels in a predetermined divided area among the plurality of divided areas,
  wherein the global reset circuit is configured to reset the electric charge accumulated by the plurality of effective pixels by outputting the global reset signal in a duration in which the reading is temporarily stopped, and set a predetermined exposure time period again, and wherein the reading timing generation circuit is configured to resume reading of the electric charge accumulated by the effective pixels in a divided area next to the predetermined divided area, reading from which is temporarily stopped.

3. The image pickup system according to claim 1, wherein the image pickup apparatus further comprises a timing generation circuit configured to generate a drive timing signal of the image pickup apparatus, and wherein the timing generation circuit is not reset by the global reset signal.

4. The image pickup system according to claim 1, wherein the information processing apparatus is configured to calculate a target illuminance value of the light source based on the brightness detection signal and control an emission amount, an emission time period, and an emission timing of the illumination light.

5. The image pickup system according to claim 1, wherein the information processing apparatus further comprises a transmission circuit configured to transmit, to the image pickup apparatus, parameters for controlling the timing of reading the electric charge accumulated by the effective pixels included in each divided area and the timing of outputting the global reset signal.

6. The image pickup system according to claim 1, wherein, when the brightness of the object is low, the information processing apparatus is configured to perform gain control or image processing of removing accumulation of electric charge by a medical treatment laser apparatus.

7. The image pickup system according to claim 4, wherein the light source comprises a lamp, and light emission from the lamp is controllable for an optional duration based on control by the information processing apparatus.

8. The image pickup system according to claim 6, wherein the information processing apparatus is configured to output, to a monitor, the image signals temporarily stored in the memory and then connected.

\* \* \* \* \*